(12) United States Patent
Ahlers et al.

(10) Patent No.: US 6,881,867 B2
(45) Date of Patent: Apr. 19, 2005

(54) METHOD FOR HYDROFORMYLATION, XANTHENE-BRIDGED LIGANDS AND CATALYST COMPRISING A COMPLEX OF SAID LIGANDS

(75) Inventors: Wolfgang Ahlers, Worms (DE); Dag Wiebelhaus, Neustadt (DE); Rocco Paciello, Bad Dürkheim (DE); Michael Bartsch, Neustadt (DE); Robert Baumann, Mannheim (DE); Dieter Vogt, Eindhoven (NL); Alison Hewat, Eindhoven (NL)

(73) Assignee: BASF Aktiengesellschaft, Ludwigshafen (DE)

( * ) Notice: Subject to any disclaimer, the term of this patent is extended or adjusted under 35 U.S.C. 154(b) by 0 days.

(21) Appl. No.: 10/380,054

(22) PCT Filed: Sep. 17, 2001

(86) PCT No.: PCT/EP01/10735

§ 371 (c)(1),
(2), (4) Date: Mar. 11, 2003

(87) PCT Pub. No.: WO02/22261

PCT Pub. Date: Mar. 21, 2002

(65) Prior Publication Data

US 2003/0195378 A1 Oct. 16, 2003

(30) Foreign Application Priority Data

Sep. 18, 2000 (DE) .......................... 100 46 026

(51) Int. Cl.[7] .......................... C07C 45/50; B01J 31/00; C07D 265/12; C07D 221/18; C07D 327/06
(52) U.S. Cl. ...................... 568/451; 568/454; 502/150; 502/158; 502/162; 502/168; 544/89; 544/338; 546/26; 549/16
(58) Field of Search .................. 568/451, 454; 502/150, 158, 162, 168; 544/89, 338; 546/26; 549/16

(56) References Cited

U.S. PATENT DOCUMENTS

| | | | |
|---|---|---|---|
| 6,265,620 B1 | 7/2001 | Urata et al. | 568/454 |
| 6,342,605 B1 | 1/2002 | Geissler et al. | 546/22 |
| 6,486,359 B1 | 11/2002 | Maas et al. | 568/454 |

FOREIGN PATENT DOCUMENTS

| | | |
|---|---|---|
| WO | 95/30680 | 11/1995 |
| WO | 99/21013 | 4/1999 |
| WO | 99/65606 | 12/1999 |

OTHER PUBLICATIONS

J.Chem.Soc.,1998 2981–2988, Goertz.
Chem.Eur.J.2001,7,No. 8, Goertz et al.
Angew.Chem.Int.Ed.1998,37,No. 22, Dierkes et al.
Organometallics 1999,18,4765–4777,van der Veen et al.
Organometallics 1995,14,3081–3089,Kranenburg et al.
Chem.Ber.124 (1991)1705–1710, Haenel et al.
Tetr.Ltrs.vol. 34,No. 13, 2017–2119, 1993, Haenel et al.
Tetr.Ltrs.vol. 36,No. 1,75–78,1995, Hillebrand et al.
Angew.Chem.2000,112,Nr.9, Selent et al., 1694–1696.
Thesis *"Zur selektiven nickelkatalysierten Hydrocyanierung von Olefinen"* (Concerning the selective nickel catalyzed hydrocyanation of olefins) 1998.

*Primary Examiner*—Johann Richter
*Assistant Examiner*—Sikarl A. Witherspoon
(74) *Attorney, Agent, or Firm*—Keil & Weinkauf

(57) ABSTRACT

In a process for the hydroformylation of ethylenically unsaturated compounds, at least one complex of a metal of transition group VIII. with at least one phosphorus-, arsenic- or antimony-containing compound as ligand is used as hydroformylation catalyst, where the compound used as ligand in each case comprises two groups which comprise a P, As or Sb atom and at least two further hetero atoms and are bound to a xanthene-like molecular framework. New compounds of this type and catalysts which comprise at least one complex of a metal of transition group VIII. with at least one such compound as ligand are also provided.

6 Claims, No Drawings

METHOD FOR HYDROFORMYLATION, XANTHENE-BRIDGED LIGANDS AND CATALYST COMPRISING A COMPLEX OF SAID LIGANDS

The present invention relates to a process for the hydroformylation of ethylenically unsaturated compounds, in which at least one complex of a metal of transition group VIII with at least one phosphorus-, arsenic- or antimony-containing compound as ligand is used as hydroformylation catalyst, where the compound used as ligand in each case comprises at least two groups which comprise a P, As or Sb atom and at least two further hetero atoms and are bound to a xanthene-like molecular framework. The invention also provides new compounds of this type and catalysts which comprise at least one complex of a metal of transition group VIII with at least one such compound as ligand.

Hydroformylation or the oxo process is an important industrial process and is employed for preparing aldehydes from olefins, carbon monoxide and hydrogen. If desired, these aldehydes can be hydrogenated by means of hydrogen in the same process step to give the corresponding oxo alcohols. The reaction itself is strongly exothermic and generally proceeds under superatmospheric pressure and at elevated temperatures in the presence of catalysts. Catalysts used are Co, Rh, Ir, Ru, Pd or Pt compounds or complexes which may be modified with N- or P-containing ligands to influence the activity and/or selectivity. The hydroformylation reaction results in formation of mixtures of isomeric aldehydes because of the possible CO addition on to each of the two carbon atoms of a double bond. In addition, double bond isomerization, i.e. shifting of internal double bonds to a terminal position and vice versa, can also occur.

Owing to the substantially greater industrial importance of α-aldehydes, optimization of the hydroformylation catalysts to achieve a very high hydroformylation activity together with a very low tendency to form double bonds not in the α position is sought. In addition, there is a need for hydroformylation catalysts which lead to good yields of α-aldehydes and in particular n-aldehydes even when internal linear olefins are used as starting materials. Here, the catalyst must make possible both the establishment of equilibrium between internal and terminal double bond isomers and the very selective hydroformylation of the terminal olefins.

The use of phosphorus-containing ligands for stabilizing and/or activating the catalyst metal in rhodium-catalyzed low-pressure hydroformylation is known. Suitable phosphorus-containing ligands are, for example, phosphines, phosphinites, phosphonites, phosphites, phosphoramidites, phospholes and phosphabenzenes. The most widespread ligands at present are triarylphosphines such as triphenylphosphine and sulfonated triphenylphosphine, since these have sufficient stability under the reaction conditions. However, a disadvantage of these ligands is that, in general, only very high ligand excesses give satisfactory yields, in particular of linear aldehydes.

In Angew. Chem. Int. Ed. 39, 1639 (2000), D. Selent et al. describe the isomerizing hydroformylation of internal olefins in the presence of rhodium catalysts, with oxyfunctionalized bisphenyl monophosphonites being used as ligands. A disadvantage of these catalysts is their low n-selectivity. Thus, in the hydroformylation of isomeric n-octenes, n-nonanal is obtained in a yield of at most 47.9%.

WO-A-98/43935 describes the use of chelating ligands in catalysts for hydroformylation.

In Tetrahedron Letters, Volume 34, No. 13, pages 2107 ff. (1993), in Tetrahedron Letters, Volume 36, No. 1, pages 75 ff. (1995) and in Chem. Ber. 124, page 1705 ff. (1991), Haenel et al. describe the synthesis of bis (diphenylphosphino)chelates having anthracene, dibenzofuran, dibenzothiophene and xanthene skeletons. The use of these compounds as catalysts is not described.

In J. Chem. Soc., Dalton Trans., 1998, pp. 2981–2988, W. Goertz et al. describe the use of chelating phosphines and phosphonites having a thioxanthene skeleton for the nickel-catalyzed hydrocyanation of styrene. Use in hydroformylation is not described.

In Organometallics 1995, 14, pages 3081 to 3089, M. Kranenburg et al. describe chelating phosphines having a xanthene skeleton and their use for regioselective rhodium-catalyzed hydroformylation. Chelating phosphonites and phosphites are not described in this document. A disadvantage of these chelating phosphines is that they are not suitable for the isomerizing hydroformylation of internal olefins with high α- or n-selectivity.

In Organometallics 1999, 18, pages 4765 to 4777, van der Veen et al. describe the use of phosphacyclic diphosphines having a xanthene skeleton as ligands for rhodium-catalyzed hydroformylation. A disadvantage of these catalysts is their very low activity which makes their use in industrial processes uneconomical.

WO 95/30680 describes bidentate phosphine ligands in which the phosphorus atoms may be bound to a xanthene skeleton and the use of these ligands in catalysts for hydroformylation. A disadvantage of these catalysts is that they are not suitable for the isomerizing hydroformylation of internal olefins with good α- or n-selectivity.

EP-A-0982314 describes bidentate carbocyclic or heterocyclic phosphine ligands and a process for preparing linear aldehydes by hydroformylation of internal olefins using such ligands. A disadvantage of these ligands is their very low activity which makes use in industrial processes uneconomical.

DE-A-19827232 describes catalysts based on monodentate, bidentate or polydentate phosphinite ligands in which the phosphorus atom and the oxygen atom of the phosphinite group are part of a 5- to 8-membered heterocycle, and their use in hydroformylation and hydrocyanation. The bidentate ligands may have a xanthene skeleton. A disadvantage of these ligands is that they are in need of improvement in terms of the α- or n-selectivity in the isomerizing hydroformylation of internal olefins.

None of the abovementioned documents describes the use of chelating phosphonites and phosphites having a xanthene skeleton as ligands in catalysts for hydroformylation.

It is an object of the present invention to provide an improved process for the hydroformylation of compounds containing at least one ethylenically unsaturated double bond. Here, a very high proportion of α-aldehydes or α-alcohols should preferably be obtained in the hydroformylation of α-olefins. In particular, the process should be suitable for the hydroformylation of internal linear olefins with high regioselectivity in favor of terminal product aldehydes. A further object of the invention is to provide new compounds and novel catalysts comprising at least one complex of a metal of transition group VIII with such a compound as ligand.

We have found that these objects are achieved by a hydroformylation process in which at least one complex of a metal of transition group VIII with at least one phosphorus-, arsenic- and/or antimony-containing compound as ligand is used as hydroformylation catalyst. This compound comprises two groups comprising a P, As and/or Sb atom, with the P, As and Sb atoms being bound directly to at least two further hetero atoms and with each of the two groups being bound to a different phenyl ring of a xanthene skeleton. The group is bound directly to the phenyl ring via the phosphorus, arsenic or antimony atom or via a hetero atom bound thereto.

The present invention accordingly provides a process for the hydroformylation of compounds containing at least one ethylenically unsaturated double bond by reaction with carbon monoxide and hydrogen in the presence of a hydroformylation catalyst comprising at least one complex of a metal of transition group VIII with at least one ligand selected from among compounds of the general formula I

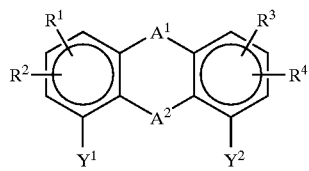

where
$A^1$ and $A^2$ are each, independently of one another, O, S, $SiR^aR^b$, $NR^c$ or $CR^5R^6$, where
  $R^a$, $R^b$, $R^c$, $R^5$ and $R^6$ are each, independently of one another, hydrogen, alkyl, cycloalkyl, heterocycloalkyl, aryl or hetaryl,
$Y^1$ and $Y^2$ are each, independently of one another, radicals containing at least one phosphorus, arsenic or antimony atom, where in each case at least two substituted or unsubstituted hetero atoms selected from among O, S and $NR^c$, where $R^c$ is hydrogen, alkyl, cycloalkyl or aryl, are directly bound to the phosphorus, arsenic or antimony atom, and
$R^1$, $R^2$, $R^3$ and $R^4$ are each, independently of one another, hydrogen, alkyl, cycloalkyl, heterocycloalkyl, aryl, hetaryl, $COOR^d$, $COO^-M^+$, $SO_3R^d$, $SO^-_3M^+$, $NE^1E^2$, $NE^1E^2E^{3+}X^-$, alkylene-$NE^1E^2E^{3+}X^-$, $OR^d$, $SR^d$, $(CHR^eCH_2O)_xR^d$, $(CH_2N(E^1))_xR^d$, $(CH_2CH_2N(E^1))_xR^d$, halogen, trifluoromethyl, nitro, acyl or cyano,
where
  $R^d$, $E^1$, $E^2$ and $E^3$ are identical or different radicals selected from among hydrogen, alkyl, cycloalkyl and aryl,
  $R^e$ is hydrogen, methyl or ethyl,
  $M^+$ is a cation,
  $X^-$ is an anion, and
  x is an integer from 1 to 120, or
$R^1$ and/or $R^3$ together with two adjacent carbon atoms of the benzene ring to which they are bound form a fused ring system having 1, 2 or 3 further rings.

For the purposes of the present invention, the expression 'alkyl' encompasses straight-chain and branched alkyl groups. They are preferably straight-chain or branched $C_1$–$C_{12}$-alkyl groups, more preferably $C_1$–$C_8$-alkyl groups and particularly preferably $C_1$–$C_4$-alkyl groups. Examples of alkyl groups are, in particular, methyl, ethyl, propyl, isopropyl, n-butyl, 2-butyl, sec-butyl, tert-butyl, n-pentyl, 2-pentyl, 2-methylbutyl, 3-methylbutyl, 1,2-dimethylpropyl, 1,1-dimethylpropyl, 2,2-dimethylpropyl, 1-ethylpropyl, n-hexyl, 2-hexyl, 2-methylpentyl, 3-methylpentyl, 4-methylpentyl, 1,2-dimethylbutyl, 1,3-dimethylbutyl, 2,3-dimethylbutyl, 1,1-dimethylbutyl, 2,2-dimethylbutyl, 3,3-dimethylbutyl, 1,1,2-trimethylpropyl, 1,2,2-trimethylpropyl, 1-ethylbutyl, 2-ethylbutyl, 1-ethyl-2-methylpropyl, n-heptyl, 2-heptyl, 3-heptyl, 2-ethylpentyl, 1-propylbutyl, octyl.

Substituted alkyl radicals preferably have 1, 2, 3, 4 or 5, in particular 1, 2 or 3, substituents selected from among cycloalkyl, aryl, hetaryl, halogen, $NE^1E^2$, $NE^1E^2E^{3+}$, carboxyl, carboxylate, —$SO_3H$ and sulfonate.

A cycloalkyl group is preferably a $C_5$–$C_7$-cycloalkyl group such as cyclopentyl, cyclohexyl and cycloheptyl.

If the cycloalkyl group is substituted, it preferably has 1, 2, 3, 4 or 5, in particular 1, 2 or 3, substituents selected from among alkyl, alkoxy and halogen.

Aryl is preferably phenyl, tolyl, xylyl, mesityl, naphthyl, anthracenyl, phenanthrenyl, naphthacenyl, in particular phenyl or naphthyl.

Substituted aryl radicals preferably have 1, 2, 3, 4 or 5, in particular 1, 2 or 3, substituents selected from among alkyl, alkoxy, carboxyl, carboxylate, trifluoromethyl, —$SO_3H$, sulfonate, $NE^1E^2$, alkylene-$NE^1E^2$, nitro, cyano and halogen.

Hetaryl is preferably pyridyl, quinolinyl, acridinyl, pyridazinyl, pyrimidinyl or pyrazinyl.

Substituted hetaryl radicals preferably have 1, 2 or 3 substituents selected from among alkyl, alkoxy, carboxyl, carboxylate, —$SO_3H$, sulfonate, $NE^1E^2$, alkylene-$NE^1E^2$, trifluoromethyl and halogen.

What has been said above in respect of alkyl, cycloalkyl and aryl radicals applies analogously to alkoxy, cycloalkyloxy and aryloxy radicals.

The radicals $NE^1E^2$ and $NE^4E^5$ are preferably N,N-dimethylamino, N,N-diethylamino, N,N-dipropylamino, N,N-diisopropylamino, N,N-di-n-butylamino, N,N-di-t-butylamino, N,N-dicyclohexylamino or N,N-diphenylamino.

Halogen is fluorine, chlorine, bromine or iodine, preferably fluorine, chlorine or bromine.

For the purposes of the present invention, carboxylate and sulfonate are preferably each a derivative of a carboxylic acid function or a sulfonic acid function, in particular a metal carboxylate or sulfonate, a carboxylic ester or sulfonic ester function or a carboxamide or sulfonamide function. These include, for example, esters of $C_1$–$C_4$-alkanoles such as methanol, ethanol, n-propanol, isopropanol, n-butanol, sec-butanol and tert-butanol.

$Y^1$ and $Y^2$ are preferably each a radical containing a phosphorus atom and in particular a radical of the formula $P(OR^7)(OR^8)$, $OP(OR^7)R^8$ or $OP(OR^7)(OR^8)$, where
$R^7$ and $R^8$ are each, independently of one another, alkyl, cycloalkyl, heterocycloalkyl, aryl or hetaryl which may bear one, two or three substituents selected from among alkyl, cycloalkyl, heterocycloalkyl, aryl, hetaryl, $COOR^f$, $COO^-M^+$, $SO_3R^f$, $SO^-_3M^+$, $NE^4E^5$, alkylene-$NE^4E^5$, $NE^4E^5E^{6+}X^-$, alkylene-$NE^4E^5E^{6+}X^-$, $OR^f$, $SR^f$, $(CHR^gCH_2O)_yR^f$, $(CH_2N(E^4))_yR^f$, $(CH_2CH_2N(E^4))_yR^f$, halogen, trifluoromethyl, nitro, acyl and cyano,
where
  $R^f$, $E^4$, $E^5$ and $E^6$ are identical or different radicals selected from among hydrogen, alkyl, cycloalkyl or aryl,
  $R^g$ is hydrogen, methyl or ethyl,
  $M^+$ is a cation,
  $X^-$ is an anion, and
  y is an integer from 1 to 120, or
$R^7$ and $R^8$ together with the phosphorus atom and the oxygen atom(s) to which they are bound form a 5- to 8-membered heterocycle to which one, two or three cycloalkyl, heterocycloalkyl, aryl or hetaryl groups may additionally be fused, where the heterocycle and, if present, the fused-on groups may each bear, independently of one another, one, two, three or four substituents selected from among alkyl, cycloalkyl, heterocycloalkyl, aryl, hetaryl, COOR$^f$, COO$^-$M$^+$, SO$_3$R$^f$, SO$^-_3$M$^+$, NE$^4$E$^5$, alkylene-NE$^4$E$^5$, NE$^4$E$^5$E$^{6+}$X$^-$, alkylene-NE$^4$E$^5$E$^{6+}$X$^-$, OR$^f$, SR$^f$, (CHR$^g$CH$_2$O)$_y$R$^f$, (CH$_2$N(E$^4$))$_y$R$^f$, (CH$_2$CH$_2$N(E$^4$))$_y$R$^f$, halogen, trifluoromethyl, nitro, acyl and cyano, where R$^f$, R$^g$, E$^4$, E$^5$, E$^6$, M$^+$, X$^-$ and y are as defined above.

In a preferred embodiment, one of the radicals Y$^1$ or Y$^2$ or both radicals Y$^1$ and Y$^2$ in the formula I are selected from among radicals of the formulae P(OR$^7$)(OR$^8$), OP(OR$^7$)R$^8$ and OP(OR$^7$)(OR$^8$) in which R$^7$ and R$^8$ together with the phosphorus atom and the oxygen atom(s) to which they are bound form a 5- to 8-membered heterocycle to which one, two or three cycloalkyl, heterocycloalkyl, aryl and/or hetaryl groups may additionally be fused, where the heterocycle and/or the fused-on groups may each, independently of one another, bear one, two, three or four substituents selected from among alkyl, alkoxy, halogen, nitro, cyano, carboxyl, SO$_3$H, sulfonate, NE$^4$E$^5$, alkylene-NE$^4$E$^5$ and carboxylate.

The radicals Y$^1$ and Y$^2$ are preferably selected from among phosphonite and/or phosphite radicals of the formula II

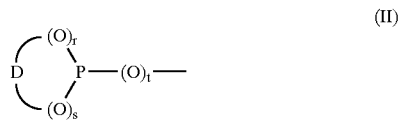

(II)

where r, s and t are each, independently of one another, 0 or 1 and the sum of r, s and t is at least 2, D together with the phosphorus atom and the oxygen atom(s) to which it is bound form a 5- to 8-membered heterocycle to which one, two or three cycloalkyl, heterocycloalkyl, aryl and/or hetaryl groups may be fused, where the fused-on groups may each bear, independently of one another, one, two, three or four substituents selected from among alkyl, alkoxy, halogen, SO$_3$H, sulfonate, NE$^4$E$^5$, alkylene-NE$^4$E$^5$, nitro, cyano, carboxyl and carboxylate, and/or D may have one, two or three substituents selected from among alkyl, alkoxy, substituted or unsubstituted cycloalkyl and substituted or unsubstituted aryl, and/or D may be interrupted by 1, 2 or 3 substituted or unsubstituted hetero atoms.

The radical D is preferably a C$_2$–C$_6$-alkylene bridge to which 1 or 2 aryl groups are fused and/or may have a substituent selected from among alkyl, substituted or unsubstituted cycloalkyl and substituted or unsubstituted aryl, and/or may be interrupted by a substituted or unsubstituted hetero atom.

The fused-on arylene of the radical D is preferably benzene or naphthalene. Fused-on benzene rings are preferably unsubstituted or have 1, 2 or 3, in particular 1 or 2, substituents selected from among alkyl, alkoxy, halogen, SO$_3$H, sulfonate, NE$^4$E$^5$, alkylene-NE$^4$E$^5$, trifluoromethyl, nitro, carboxyl, alkoxycarbonyl, acyl and cyano. Fused-on naphthalenes are preferably unsubstituted or have 1, 2 or 3, in particular 1 or 2, of the substituents mentioned above for the fused-on benzene rings in the ring which is not fused on and/or in the fused-on ring. An alkyl substituent on the fused-on aryls is preferably C$_1$–C$_4$-alkyl and in particular methyl, isopropyl or tert-butyl. Alkoxy is preferably C$_1$–C$_4$-alkoxy and in particular methoxy. Alkoxycarbonyl is preferably C$_1$–C$_4$-alkoxycarbonyl. Halogen is particularly preferably fluorine or chlorine.

If the C$_2$–C$_6$-alkylene bridge of the radical D is interrupted by 1, 2 or 3 substituted or unsubstituted hetero atoms, these are preferably selected from among O, S and NR$^h$, where R$^h$ is alkyl, cycloalkyl or aryl. The C$_2$–C$_6$-alkylene bridge of the radical D is preferably interrupted by one substituted or unsubstituted hetero atom.

If the C$_2$–C$_6$-alkylene bridge of the radical D is substituted, it preferably has 1, 2 or 3, in particular 1, substituents selected from among alkyl, cycloalkyl and aryl, where the aryl substituent may bear 1, 2 or 3 of the substituents mentioned for aryl. The alkylene bridge D preferably has one substituent selected from among methyl, ethyl, isopropyl, phenyl, p-(C$_1$–C$_4$-alkyl)phenyl, preferably p-methylphenyl, p-(C$_1$–C$_4$-alkoxy)phenyl, preferably p-methoxyphenyl, p-halophenyl, preferably p-chlorophenyl, and p-trifluoromethylphenyl.

The radical D is preferably a C$_3$–C$_6$-alkylene bridge which is fused and/or substituted and/or interrupted by substituted or unsubstituted hetero atoms as described above. In particular, the radical D is a C$_3$–C$_6$-alkylene bridge on to which one or two phenyl and/or naphthyl groups are fused, where the phenyl or naphthyl groups may bear 1, 2 or 3, in particular 1 or 2, of the abovementioned substituents.

Preference is given to the radical D (i.e. R$^7$ and R$^8$ together) together with the phosphorus atom and the oxygen atom(s) to which it is bound forming a 5- to 8-membered heterocycle, with the radical D (R$^7$ and R$^8$ together) being a radical selected from among the radicals of the formulae II.1 to II.5,

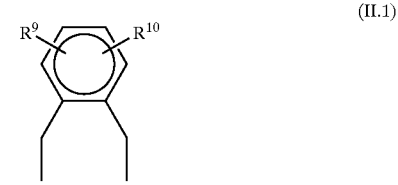

(II.1)

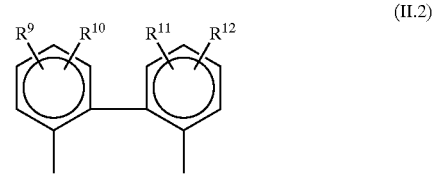

(II.2)

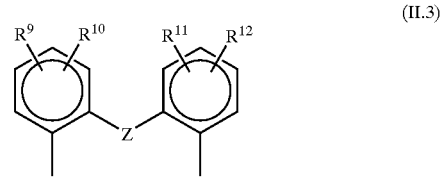

(II.3)

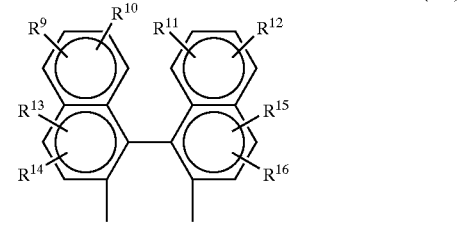

(II.4)

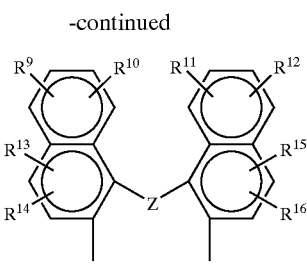
(II.5)

where
z is O, S or NR$^i$, where
R$^i$ is alkyl, cycloalkyl or aryl,
or Z is a C$_1$–C$_3$-alkylene bridge which may have a double bond and/or an alkyl, cycloalkyl or aryl substituent, where the aryl substituent may bear one, two or three of the substituents mentioned for aryl,
or Z is a C$_2$–C$_3$-alkylene bridge which is interrupted by O, S or NR$^i$,
R$^9$, R$^{10}$, R$^{11}$, R$^{12}$, R$^{13}$, R$^{14}$, R$^{15}$ and R$^{16}$ are each, independently of one another, hydrogen, alkyl, cycloalkyl, aryl, alkoxy, halogen, SO$_3$H, sulfonate, NE$^4$E$^5$, alkylene-NE$^4$E$^5$, trifluoromethyl, nitro, alkoxycarbonyl, carboxyl or cyano.

D is preferably a radical of the formula II.1 in which R$^9$ and R$^{10}$ are each hydrogen.

D is preferably a radical of the formula II.2a

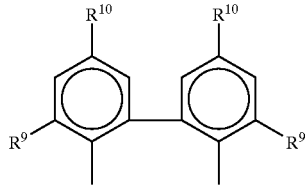
(II.2a)

where
R$^9$ is hydrogen, C$_1$–C$_4$-alkyl, C$_1$–C$_4$-alkoxy, SO$_3$H, sulfonate, NE$^4$E$^5$, alkylene-NE$^4$E$^5$, preferably hydrogen, C$_1$–C$_4$-alkyl or C$_1$–C$_4$-alkoxy, in particular methyl, methoxy, isopropyl or tert-butyl,
R$^{10}$ is hydrogen, C$_1$–C$_4$-alkyl, preferably methyl, isopropyl or tert-butyl, C$_1$–C$_4$-alkoxy, preferably methoxy, fluorine, chlorine or trifluoromethyl. R$^{10}$ may also be SO$_3$H, sulfonate, NE$^4$E$^5$ or alkylene-NE$^4$E$^5$.

D is prefeably a radical of the formula II.3a

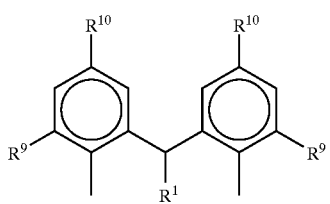
(II.3a)

where
R$^9$ and R$^{10}$ are as defined for the formula II.2a,
R$^1$ is hydrogen, C$_1$–C$_4$-alkyl, preferably methyl or ethyl, phenyl, p-(C$_1$–C$_4$-alkoxy)phenyl, preferably p-methoxyphenyl, p-fluorophenyl, p-chlorophenyl or p-(trifluoromethyl)phenyl.

D is preferably a radical of the formula II.4 in which R$^9$, R$^{10}$, R$^{11}$, R$^{12}$, R$^{13}$, R$^{14}$, R$^{15}$ and R$^{16}$ are each hydrogen.

D is preferably a radical of the formula II.4 in which R$^9$, R$^{10}$, R$^{11}$, R$^{12}$, R$^{14}$ and R$^{16}$ are each hydrogen and the radicals R$^{13}$ and R$^{15}$ are each, independently of one another, alkoxycarbonyl, preferably methoxycarbonyl, ethoxycarbonyl, n-propyloxycarbonyl or isopropyloxycarbonyl. In particular, the radicals R$^{13}$ and R$^{15}$ are located in the ortho position relative to the phosphorus atom or oxygen atom.

D is preferably a radical of the formula II.5 in which R$^9$, R$^{10}$, R$^{11}$, R$^{12}$, R$^{13}$, R$^{14}$, R$^{15}$ and R$^{16}$ are each hydrogen and Z is CR$^i$, where R$^1$ is as defined above.

D is preferably a radical of the formula II.5 in which R$^9$, R$^{10}$, R$^{11}$, R$^{12}$, R$^{14}$ and R$^{16}$ are each hydrogen, Z is CR$^h$ and the radicals R$^{13}$ and R$^{15}$ are each, independently of one another, alkoxycarbonyl, preferably methoxycarbonyl, ethoxycarbonyl, n-propyloxycarbonyl or isopropyloxycarbonyl. In particular, the radicals R$^{13}$ and R$^{15}$ are located in the ortho position relative to the phosphorus atom or oxygen atom.

In a further, preferred embodiment, one of the radicals Y$^1$ or Y$^2$ or both radicals Y$^1$ and Y$^2$ in the formula I are selected from among radicals of the formulae P(OR$^7$)(OR$^8$), OP(OR$^7$)R$^8$ and OP(OR$^7$)(OR$^8$) in which R$^7$ and R$^8$ do not together form a heterocycle.

The radicals R$^7$ and R$^8$ are preferably each, independently of one another, alkyl, aryl or hetaryl which may bear one, two or three substituents selected from among alkyl (only for aryl or hetaryl), cycloalkyl, aryl, alkoxy, cycloalkoxy, aryloxy, halogen, trifluoromethyl, nitro, cyano, carboxyl, carboxylate, acyl, —SO$_3$H, sulfonate, NE$^4$E$^5$ and alkylene-NE$^4$E$^5$, where E$^4$ and E$^5$ are identical or different and are selected from among alkyl, cycloalkyl and aryl.

The radicals R$^7$ and R$^8$ are preferably selected independently from among the radicals of the formulae II.6 and II.7

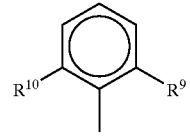
(II.6)

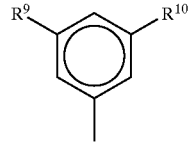
(II.7)

where
R$^9$ and R$^{10}$ are each, independently of one another, hydrogen, C$_1$–C$_4$-alkyl, COOR$^f$, COO$^-$M$^+$, SO$_3$R$^d$, SO$_3^-$M$^+$, NE$^4$E$^5$, alkylene-NE$^4$E$^5$, NE$^4$E$^5$E$^{6+}$X$^-$, alkylene-NE$^4$E$^5$E$^{6+}$X$^-$, C$_1$–C$_4$-alkoxy, halogen or trifluoromethyl, where R$^f$, E$^4$, E$^5$ and E$^6$ may be identical or different and are each hydrogen, alkyl, cycloalkyl or aryl, M$^+$ is a cation and X$^-$ is an anion.

In the formulae II.6 and II.7, the radicals R$^9$ and R$^{10}$ are preferably each, independently of one another, hydrogen, C$_1$–C$_4$-alkyl or C$_1$–C$_4$-alkoxy, in particular methyl, methoxy, isopropyl or tert-butyl.

A$^1$ and A$^2$ are preferably each, independently of one another, O, S and CR$^5$R$^6$, where R$^5$ and R$^6$ are each, independently of one another, hydrogen, alkyl, cycloalkyl, aryl or hetaryl. In particular, R$^5$ and R$^6$ are each, independently of one another, hydrogen or C$_1$–C$_4$-alkyl such as methyl, ethyl, n-propyl, n-butyl or tert-butyl. In particular, R$^5$ and R$^6$ are both methyl.

Preference is given to one of the radicals A$^1$ or A$^2$ being O or S and the other being CR$^5$R$^6$. More preferably, the radicals A$^1$ and A$^2$ are selected from among O and S.

The radicals $R^1$, $R^2$, $R^3$ and $R^4$ are preferably selected from among hydrogen, alkyl, cycloalkyl, aryl and hetaryl. Preference is given to $R^1$ and $R^3$ being hydrogen and $R^2$ and $R^4$ being $C_1$–$C_4$-alkyl such as methyl, ethyl, n-propyl, n-butyl or tert-butyl.

At least one of the radicals $R^1$, $R^2$, $R^3$ and/or $R^4$ is preferably a polar (hydrophilic) group, which then generally results in water-soluble catalysts. The polar groups are preferably selected from among $COOR^d$, $COO^-M^+$, $SO_3R^d$, $SO^-_3M^+$, $NE^1E^2$, alkylene-$NE^1E^2$, $NE^1E^2E^{3+}X^-$, alkylene-$NE^1E^2E^{3+}X^-$, $OR^d$, $SR^d$, $(CHR^eCH_2O)_xR^d$ or $(CH_2CH_2N(E^1))_xR^d$, where $R^d$, $E^1$, $E^2$, $E^3$, $R^d$, $R^e$, $M^+$, $X^-$ and x are as defined above.

$R^1$, $R^2$, $R^3$ and $R^4$ are particularly preferably each hydrogen.

If $R^1$ and/or $R^3$ form a fused-on ring system, the fused-on groups are preferably benzene or naphthalene groups. Fused-on benzene rings are preferably unsubstituted or have 1, 2 or 3, in particular 1 or 2, substituents selected from among alkyl, alkoxy, halogen, $SO_3H$, sulfonate, $NE^4E^5$, alkylene-$NE^4E^5$, trifluoromethyl, nitro, carboxyl, alkoxycarbonyl, acyl and cyano. Fused-on naphthalenes are preferably unsubstituted or have 1, 2, or 3, in particular 1 or 2, of the substituents mentioned above for the fused-on benzene rings in the ring which is not fused on and/or in the fused-on ring.

$M^+$ is preferably an alkali metal cation, e.g. $Li^+$, $Na^+$ or $K^+$, $NH_4^+$ or a quarternary ammonium compound as is obtainable by protonation or quaternization of amines.

$X^-$ is preferably halide, particularly preferably $Cl^-$ or $Br^-$.

In a preferred embodiment of the process of the present invention, use is made of a hydroformylation catalyst in which the compound of the formula I is selected from among the compounds of the formulae I.1 to I.6

(I.1)

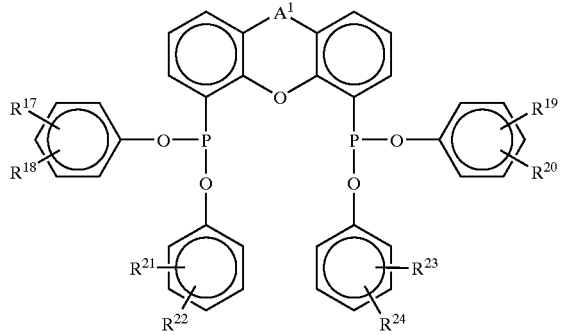

(I.2)

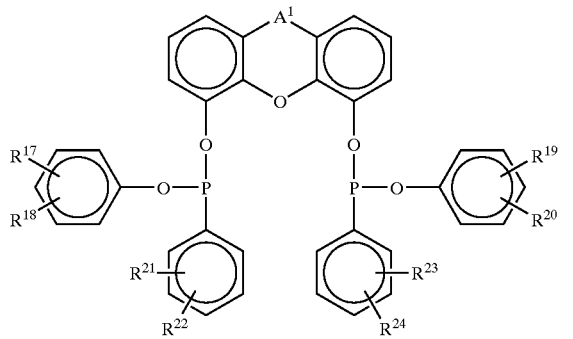

(I.3)

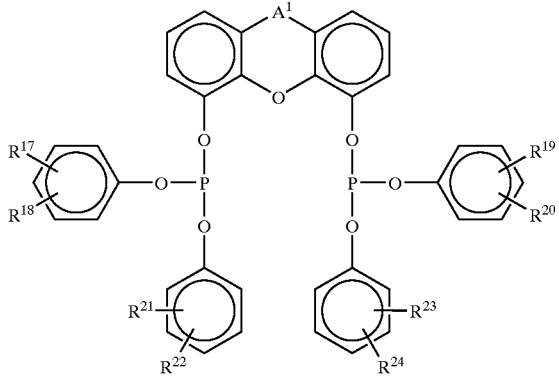

(I.4)

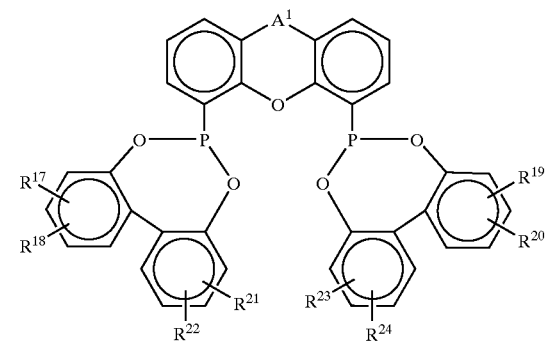

(I.5)

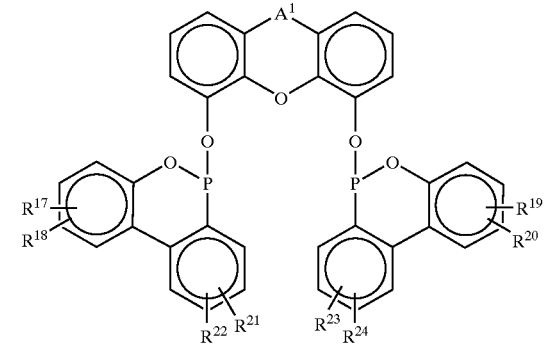

(I.6)

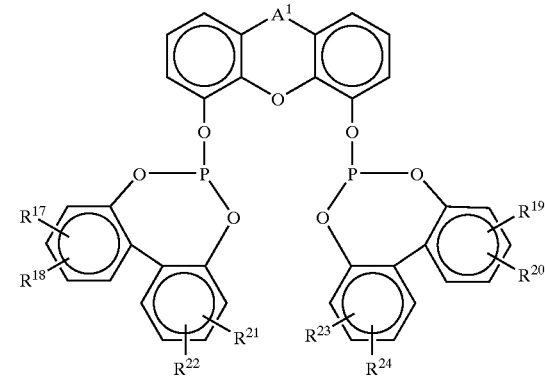

where $A^1$ is O, S or $CR^5R^6$, where $R^5$ and $R^6$ are each, independently of one another, hydrogen or $C_1$–$C_4$-alkyl, in particular methyl or tert-butyl, $R^{17}$, $R^{18}$, $R^{19}$, $R^{20}$, $R^{21}$, $R^{22}$, $R^{23}$ and $R^{24}$ are each, independently of one another,
hydrogen, alkyl, preferably $C_1$–$C_4$-alkyl, in particular methyl or tert-butyl, cycloalkyl, heterocycloalkyl, aryl, hetaryl, $COOR^d$, $COO^-M^+$, $SO_3R^f$, $SO^-_3M^+$, $NE^4E^5$, alkylene-$NE^4E^5$, $NE^4E^5E^{6+}X^-$, alkylene-$NE^4E^5E^{6+}X^-$, $OR^f$, preferably $C_1$–$C_4$-alkoxy, in particular methoxy, $SR^f$, $(CHR^gCH_2O)_yR^f$, $(CH_2N(E^4))_yR^f$, $(CH_2CH_2N(E^4))_yR^f$, halogen, trifluoromethyl, nitro, acyl and cyano,
where
$R^f$, $E^4$, $E^5$ and $E^6$ are identical or different radicals selected from among hydrogen, alkyl, preferably $C_1$–$C_4$-alkyl, in particular methyl or tert-butyl, alkoxy, preferably methoxy, cycloalkyl and aryl,
$R^g$ is hydrogen, methyl or ethyl,
$M^+$ is a cation,
$X^-$ is an anion, and
y is an integer from 1 to 120.

The invention further provides compounds of the formula I

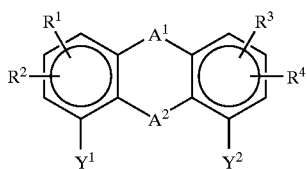

where
$A^1$ and $A^2$ are each, independently of one another, O, S, $SiR^aR^b$, $NR^c$ or $CR^5R^6$, with the exception of $A^1$=S and $A^2$=O, where
$R^a$, $R^b$, $R^c$, $R^5$ and $R^6$ are each, independently of one another, hydrogen, alkyl, cycloalkyl, heterocycloalkyl, aryl or hetaryl,
$Y^1$ and $Y^2$ are each, independently of one another, radicals containing at least one phosphorus, arsenic or antimony atom, where in each case at least two substituted or unsubstituted heteroatoms selected from among O, S and $NR^c$, where $R^c$ is hydrogen, alkyl, cycloalkyl or aryl, are directly bound to the phosphorus, arsenic or antimony atom, and
$R^1$, $R^2$, $R^3$ and $R^4$ are each, independently of one another, hydrogen, alkyl, cycloalkyl, heterocycloalkyl, aryl, hetaryl, $COOR^d$, $COO^-M^+$, $SO_3R^d$, $SO^-_3M^+$, $NE^1E^2$, $NE^1E^2E^{3+}X^-$, alkylene-$NE^1E^2E^{3+}X^-$, $OR^d$, $SR^d$, $(CHR^eCH_2O)_xR^d$, $(CH_2N(E^1))_xR^d$, $(CH_2CH_2N(E^1))_xR^d$, halogen, trifluoromethyl, nitro, acyl or cyano,
where
$R^d$, $E^1$, $E^2$ and $E^3$ are identical or different radicals selected from among hydrogen, alkyl, cycloalkyl and aryl,
$R^e$ is hydrogen, methyl or ethyl,
$M^+$ is a cation,
$X^-$ is an anion, and
x is an integer from 1 to 120, or $R^1$ and/or $R^3$ together with two adjacent carbon atoms of the benzene ring to which they are bound form a fused ring system having 1, 2 or 3 further rings.

As regards preferred embodiments of the compounds of the formula I, reference may be made to what has been said above in respect of the ligands of the formula I used in the hydroformylation process of the present invention.

The invention further provides a catalyst comprising at least one complex of a metal of transition group VIII with at least one novel compound of the formula I as defined above.

The catalysts of the present invention and those used according to the present invention may comprise one or more of the compounds of the formula I as ligands. In addition to the above-described ligands of the formula I, they may further comprise at least one additional ligand selected from among halides, amines, carboxylates, acetylacetonate, arylsulfonates and alkylsulfonates, hydride, CO, olefins, dienes, cycloolefins, nitriles, N-containing heterocycles, aromatics and heteroaromatics, ethers, $PF_3$, phospholes, phosphabenzenes and monodentate, bidentate and polydentate phosphine, phosphinite, phosphonite, phosphoramidite and phosphite ligands.

The metal of transition group VIII is preferably cobalt, ruthenium, rhodium, palladium, platinum, osmium or iridium, in particular cobalt, rhodium, ruthenium or iridium.

The preparation of the compounds of the formula I used according to the present invention and the novel compounds of the formula I can be carried out, for example, starting from a compound of the formula I.a

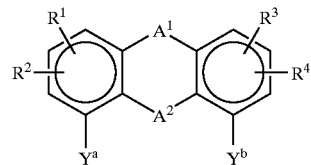

where
$Y^a$ and $Y^b$ are each, independently of one another, a radical $Y^1$ or $Y^2$ as defined above, or $Y^a$ and $Y^b$ are each, independently of one another, halogen, OH, $OC(O)CF_3$ or $SO_3Me$ where Me=hydrogen, Li, Na or K, and $Y^a$ and/or $Y^b$ may also be hydrogen if at least one of the radicals $R^2$ and/or $R^4$ is hydrogen, an alkoxy group or an alkoxycarbonyl group located in the ortho position relative to $Y^a$ and/or $Y^b$, and
$A^1$, $A^2$, $R^1$, $R^2$, $R^3$ and $R^4$ are as defined above.

The functionalization of the radicals $Y^a$ and $Y^b$ to form the radicals $Y^1$ and $Y^2$ can be carried out in a manner analogous to known methods. For example, compounds of the formula I.a in which $Y^a$ and $Y^b$ are halogen, preferably chlorine, can firstly be lithiated and the intermediate formed can be reacted with a compound which bears a halogen atom, preferably a chlorine atom, on the phosphorus atom, for example a compound of the formula Cl-P$(OR^7)_2$, Cl-P$(OR^7)(OR^8)$ or Cl-P$(OR^7)_2$. The novel compounds I in which $Y^1$ and $Y^2$ are each a radical of the formula II in which t=0 are prepared by, for example, reaction of I.a with compounds of the formula II.a according to the following scheme,

where r, s and D are as defined above for the compounds of the formula II.

In place of compounds of the formula I.a in which $Y^a=Y^b$=halogen, it is also possible to lithiate compounds I.a in which $Y^a=Y^b$=hydrogen and in which hydrogen, an alkoxy group or an alkoxycarbonyl group is present in each of the ortho positions relative to $Y^a$ and $Y^b$. Such reactions are described in the literature under the name "Ortho-Lithiation" (see, for example, D. W. Slocum, J. Org. Chem., 1976, 41, 3652–3654; J. M. Mallan, R. L. Bebb, Chem. Rev., 1969, 693 ff; V. Snieckus, Chem. Rev., 1980, 6, 879–933). The organolithium compounds obtained in this way can then be reacted with the phosphorus halide compounds in the manner indicated above to form the target compounds I.

The arsenic compounds I and the antimony compounds I can be prepared in an analogous way.

In general, the catalysts or catalyst precursors used in each case are converted under hydroformylation conditions into catalytically active species of the formula $H_xM_y(CO)_zL_q$, where M is a metal of transition group VIII, L is a phosphorus-, arsenic- or antimony-containing compound of the formula I and q, x, y, z are integers which depend on the valence and type of the metal and also the number of coordination positions occupied by the ligand L. z and q are preferably, independently of one another, at least 1, e.g. 1, 2 or 3. The sum of z and q is preferably from 2 to 5. If desired, the complexes may further comprise at least one of the above-described additional ligands.

In a preferred embodiment, the hydroformylation catalysts are prepared in situ in the reactor used for the hydroformylation reaction. However, if desired, the catalysts used according to the present invention can also be prepared separately and isolated by customary methods. To prepare the catalysts used according to the present invention in situ, it is possible, for example, to react at least one compound of the formula I, a compound or a complex of a metal of transition group VIII, if desired at least one further additional ligand and, if desired, an activating agent in an inert solvent under the hydroformylation conditions.

Suitable rhodium compounds or complexes are, for example, rhodium(II) and rhodium(III) salts, e.g. rhodium (III) chloride, rhodium(III) nitrate, rhodium(III) sulfate, potassium rhodium sulfate, rhodium(II) and rhodium(III) carboxylates, rhodium(II) and rhodium(III) acetate, rhodium (III) oxide, salts of rhodic(III) acid, trisammonium hexachlororhodate(III), etc. Also suitable are rhodium complexes such as dicarbonylrhodium acetylacetonate, acetylacetonatobisethylenerhodium(I), etc. Preference is given to using dicarbonylrhodium acetylacetonate or rhodium acetate.

Ruthenium salts or compounds are likewise suitable. Suitable ruthenium salts are, for example, ruthenium(III) chloride, ruthenium(IV), ruthenium(VI) or ruthenium(VIII) oxide, alkali metal salts of ruthenium oxo acids such as $K_2RuO_4$ or $KRuO_4$ or complexes such as $RuHCl(CO)(PPh_3)_3$. It is also possible to use the carbonyls of ruthenium, e.g. dodecacarbonyltriruthenium or octadecacarbonylhexaruthenium, or mixed forms in which Co has been partially replaced by ligands of the formula $PR_3$, e.g. $Ru(CO)_3(PPh_3)_2$, in the process of the present invention.

Suitable cobalt compounds are, for example cobalt(II) chloride, cobalt(II) sulfate, cobalt(II) carbonate, cobalt(II) nitrate, their amine or hydrate complexes, cobalt carboxylates such as cobalt acetate, cobalt ethylhexanoate, cobalt naphthanoate, and also the caprolactamate complex of cobalt. Here too, the carbonyl complexes of cobalt, e.g. octacarbonyldicobalt, dodecacarbonyltetracobalt and hexadecacarbonylhexacobalt, can be used.

The abovementioned and further suitable compounds of cobalt, rhodium, ruthenium and iridium are known in principle and are adequately described in the literature or they can be prepared by a person skilled in the art using methods analogous to those for known compounds.

Suitable activating agents are, for example, Brönsted acids, Lewis acids, e.g. $BF_3$, $AlCl_3$, $ZnCl_2$, and Lewis bases.

As solvents, preference is given to using the aldehydes which are formed in the hydroformylation of the respective olefins, and also their higher-boiling downstream reaction products, e.g. the products of the aldol condensation. Further suitable solvents are aromatics such as toluene and xylenes, hydrocarbons or mixtures of hydrocarbons, also for dilution of the abovementioned aldehydes and the downstream products of the aldehydes. Further solvents are esters of aliphatic carboxylic acids with alkanoles, for example ethyl acetate or Texanol™, ethers such as tert-butyl methyl ether and tetrahydrofuran. In the case of sufficiently hydrophilic ligands, it is also possible to use alcohols such as methanol, ethanol, n-propanol, isopropanol, n-butanol, isobutanol, ketones, such as acetone and methyl ethyl ketone etc.

"Ionic liquids" can also be used as solvents. These are liquid salts, for example N,N'-dialkylimidazolium salts such as N-butyl-N'-methylimidazolium salts, tetraalkylammonium salts such as tetra-n-butylammonium salts, N-alkylpyridinium salts such as n-butylpyridinium salts, tetraalkylphosphonium salts such as trishexyl(tetradecyl) phosphonium salts, e.g. the tetrafluoroborates, acetates, tetrachloroaluminates, hexafluorophosphates, chlorides and tosylates.

Furthermore, the reactions can also be carried out in water or aqueous solvent systems comprising water together with a water-miscible solvent, for example an alcohol such as methanol, ethanol, n-propanol, isopropanol, n-butanol, isobutanol, a ketone such as acetone or methyl ethyl ketone or another solvent. For this purpose, use is made of ligands of the formula I which have been modified with polar groups, for example ionic groups such as $SO_3Me$, $CO_2Me$ where Me=Na, K or $NH_4$, or such as $N(CH_3)_3^+$. The reactions then occur as a two-phase catalysis in which the catalyst is present in the aqueous phase and starting materials and products form the organic phase. The reaction in the "ionic liquids" can also be carried out as a two-phase catalysis.

The molar ratio of phosphorus-containing ligand to metal of transition group VIII is generally in a range from about 1:1 to 1000:1.

Suitable substrates for the hydroformylation process of the present invention are in principle all compounds which contain one or more ethylenically unsaturated double bonds. These include, for example, olefins such as α-olefins, internal straight-chain and internal branched olefins. Suitable α-olefins are, for example, ethylene, propene, 1-butene, 1-pentene, 1-hexene, 1-heptene, 1-octene, 1-nonene, 1-decene, 1-undecene, 1-dodecene, etc.

Preferred branched, internal olefins are $C_4$–$C_{20}$-olefins such as 2-methyl-2-butene, 2-methyl-2-pentene, 3-methyl-2-pentene, branched, internal heptene mixtures, branched, internal octene mixtures, branched, internal nonene mixtures, branched, internal decene mixtures, branched, internal undecene mixtures, branched, internal dodecene mixtures, etc.

Further suitable olefins for the hydroformylation are $C_5$–$C_8$-cycloalkenes such as cyclopentene, cyclohexene, cycloheptene, cyclooctene and their derivatives, e.g. their $C_1$–$C_{20}$-alkyl derivatives having from 1 to 5 alkyl substituents. Olefins suitable for hydroformylation also include vinyl aromatics such as styrene, α-methylstyrene, 4-isobutylstyrene, etc. Other suitable olefins for the hydroformylation are α,β-ethylenically unsaturated monocarboxylic and/or dicarboxylic acids, their esters, monoesters and amides, e.g. acrylic acid, methacrylic acid, maleic acid, fumaric acid, crotonic acid, itaconic acid, methyl 3-penteneoate, methyl 4-penteneoate, methyl oleate, methyl acrylate, methyl methacrylate, unsaturated nitriles such as 3-pentenenitrile, 4-pentenenitrile, acrylonitrile, vinyl ethers such as vinyl methyl ether, vinyl ethyl ether, vinyl propyl ether, etc., $C_1$–$C_{20}$-alkenols, -alkenediols and -alkadienoles, e.g. 2,7-octadien-1-ol. Further suitable substrates are dienes or polyenes containing isolated or conjugated double bonds. These include, for example, 1,3-butadiene, 1,4-pentadiene, 1,5-hexadiene, 1,6-heptadiene, 1,7-octadiene, vinylcyclohexene, dicyclopentadiene, 1,5,9-cyclooctatriene and also homopolymers and copolymers of butadiene.

The unsaturated compound used for the hydroformylation is preferably selected from among internal linear olefins and olefin mixtures in which at least one internal linear olefin is present. Preferred linear (straight-chain) internal olefins are $C_4$–$C_{20}$-olefins such as 2-butene, 2-pentene, 2-hexene, 3-hexene, 2-heptene, 3-heptene, 2-octene, 3-octene, 4-octene, etc., and mixtures thereof.

In the hydroformylation process of the present invention, preference is given to using an olefin mixture which is available on an industrial scale and comprises, in particular, at least one internal linear olefin. These include, for example, the Ziegler olefins obtained by controlled ethene oligomerization in the presence of alkylaluminum catalysts. These are essentially unbranched olefins having a terminal double bond and an even number of carbon atoms. Further examples are the olefins obtained by ethene oligomerization in the presence of various catalyst systems, e.g. the predominantly linear α-olefins obtained in the presence of alkylaluminum chloride/titanium tetrachloride catalysts and the α-olefins obtained by the Shell Higher Olefin Process (SHOP) in the presence of nickel-phosphine complexes as catalysts. Further suitable industrially available olefin mixtures are obtained in the paraffin dehydrogenation of appropriate petroleum fractions, e.g. kerosene or diesel oil fractions. To convert paraffins, predominantly n-paraffins, into olefins, essentially three processes are used:

thermal cracking (steam cracking), catalytic dehydrogenation and chemical dehydrogenation by chlorination and dehydrochlorination.

Thermal cracking leads predominantly to α-olefins, while the other variants produce olefin mixtures which generally also have relatively high proportions of olefins containing an internal double bond. Further suitable olefin mixtures are the olefins obtained in metathesis or telomerization reactions. They include, for example, the olefins from the Phillips triolefin process, a modified SHOP comprising ethylene oligomerization, double bond isomerization and subsequent metathesis (ethenolysis).

Further suitable industrial olefin mixtures which can be used in the hydroformylation process of the present invention are selected from among dibutenes, tributenes, tetrabutenes, dipropenes, tripropenes, tetrapropenes, mixtures of butene isomers, in particular raffinate II, dihexenes, dimers and oligomers from the Dimersol® process of IFP, the Octol® process of Hüls, the Polygas process, etc.

Preference is given to a process in which the hydroformylation catalyst is prepared in situ by reacting at least one compound of the formula I, a compound or a complex of a metal of transition group VIII and, if desired, an activating agent in an inert solvent under the hydroformylation conditions.

The hydroformylation reaction can be carried out continuously, semicontinuously or batchwise.

Suitable reactors for the continuous reaction are known to those skilled in the art and are described, for example, in Ullmanns Enzyklopädie der technischen Chemie, Vol. 1, 3rd Edition, 1951, p. 743 ff.

Suitable pressure-rated reactors are likewise known to those skilled in the art and are described, for example, in Ullmanns Enzyklopädie der technischen Chemie, Vol. 1, 3rd Edition, 1951, p. 769 ff. In general, the process of the present invention is carried out using an autoclave which may, if desired, be provided with a stirrer and an internal lining.

The composition of the synthesis gas comprising carbon monoxide and hydrogen used in the process of the present invention can vary within a wide range. The molar ratio of carbon monoxide to hydrogen is generally from about 5:95 to 70:30, preferably from about 40:60 to 60:40. Particular preference is given to using a molar ratio of carbon monoxide to hydrogen in the region of about 1:1.

The temperature in the hydroformylation reaction is generally in a range from about 20 to 180° C., preferably from about 50 to 150° C. The reaction is generally carried out at the partial pressure of the reaction gas at the reaction temperature chosen. The pressure is generally in a range from about 1 to 700 bar, preferably from 1 to 600 bar, in particular from 1 to 300 bar. The reaction pressure can be varied as a function of the activity of the hydroformylation catalyst used. In general, the catalysts based on phosphorus-, arsenic- or antimony-containing compounds which are used according to the present invention allow reaction in a low pressure range, for example in the range from 1 to 100 bar.

The hydroformylation catalysts of the present invention and those used according to the present invention can be separated from the output from the hydroformylation reaction by customary methods known to those skilled in the art and can generally be reused for the hydroformylation.

The above-described novel catalysts which comprise chiral compounds of the formula I are suitable for enantioselective hydroformylation.

The above-described catalysts can also be immobilized on a suitable support, e.g. made of glass, silica gel, synthetic resins, etc., in a suitable manner, e.g. by binding via functional groups suitable as anchor groups, adsorption, grafting, etc. They are then also suitable for use as solid-phase catalysts.

Surprisingly, the hydroformylation activity of catalysts based on phosphine ligands of the formula I is generally higher than the activity in respect of isomerization to form internal double bonds. The catalysts of the present invention and those used according to the present invention advantageously display a high selectivity to α-aldehydes or α-alcohols in the hydroformylation of α-olefins. In addition, the hydroformylation of internal linear olefins (isomerizing hydroformylation) generally also gives good yields of α-aldehydes or -alcohols and in particular n-aldehydes or -alcohols. Furthermore, these catalysts generally have a high stability under hydroformylation conditions, so that they generally make it possible to achieve longer catalyst operating lives than are achieved using the catalysts based on conventional chilating ligands known from the prior art. Furthermore, the catalysts of the present invention and those used according to the present invention advantageously display a high activity, so that the corresponding aldehydes or alcohols are generally obtained in good yields. In the hydroformylation of α-olefins and also of internal, linear olefins, they also display a very low selectivity to the hydrogenation product of the olefin used.

The invention further provides for the use of catalysts comprising at least one complex of a metal of transition group VIII with at least one compound of the formula I, as described above, for hydroformylation, carbonylation and hydrogenation.

The invention is illustrated by the nonrestrictive examples below.

EXAMPLES

The following ligands were used for hydroformylation:

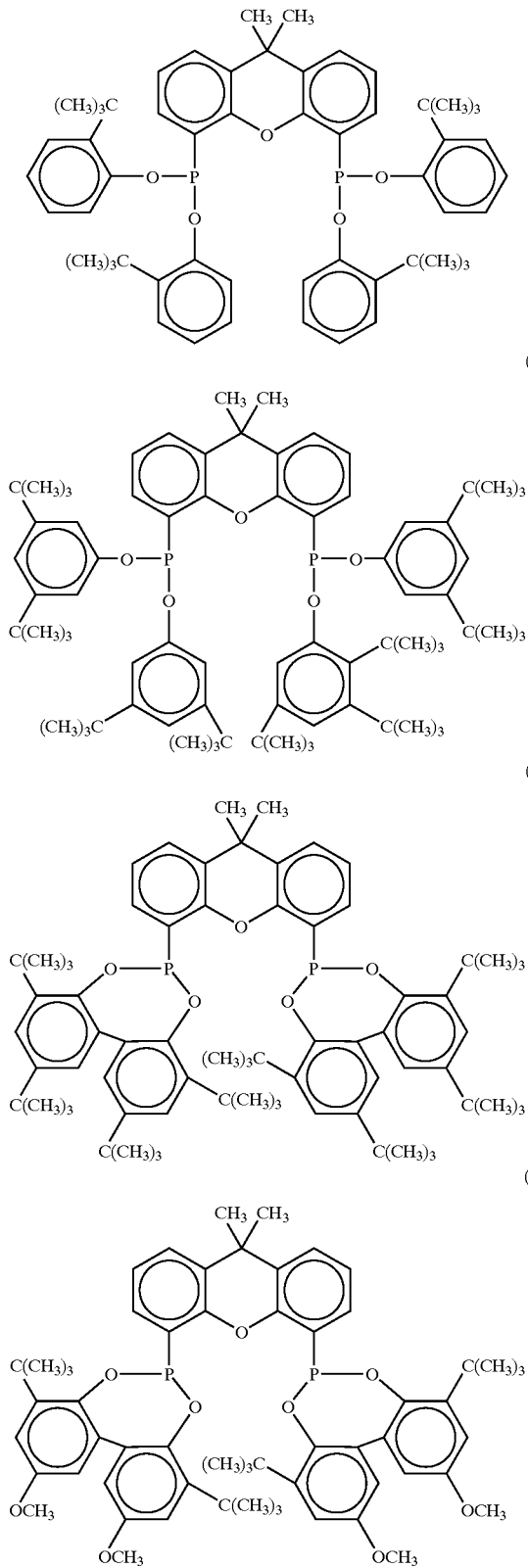

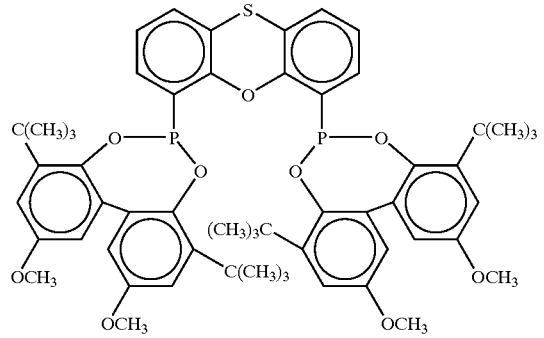

I. Preparation of the Ligands
I.1 Preparation of Ligand D
Preparation of 2,2'-dihydroxy-3,3'-di-tert-butyl-5,5'-dimethoxy-1, 1'-biphenyl In a 1000 ml flask fitted with dropping funnel and large egg-shaped stirrer, 10 g of 3-tert-butyl-4-hydroxyanisole are dissolved in 300 ml of methanol. Over the course of one hour, a solution of 1.07 g of KOH and 18.3 g of $K_3(Fe(CN)_6)$ in 300 ml of water is added dropwise. As the point of introduction, the solution becomes blue and the mixture acquires a pink mother-of-pearl color with salt precipitation. The mixture is stirred for another two hours at room temperature. 200 ml of water are then added, resulting in partial dissolution of the white precipitate. The suspension is transferred to a 2 l separating funnel and extracted twice with 500 ml each time of ethyl acetate. The aqueous solution is extracted once with 150 ml of ether and the combined organic phases are washed with 200 ml of saturated NaCl solution and dried over $Na_2SO_4$. Removal of the solvent on a rotary evaporator gives 9.8 g of a light-brown solid. Washing the crude product with n-hexane gives a white powder. The yield based on the light-brown powder was 100% of theory.

Preparation of dibenzo[d,f]-2,2'-di-tert-butyl-4,4'-dimethoxy-[1,3,2]-dioxyphosphochloride The 2,2'-dihydroxy-3,3'-di-tert-butyl-5,5'-dimethoxy-1,1'-biphenyl was freed of oxidation products by washing with small amounts of ethyl acetate. 10 g (27.9 mmol) of the biphenyl were placed in a 500 ml flask fitted with a condenser and dried azeotropically three times using 10 ml of toluene each time and subsequently dissolved in 110 ml of toluene. A catalytic amount (0.24 g) of N-methylpyrrolidone (NMP) was subsequently added. One equivalent of $PCl_3$ (6.29 g) was added via a septum. The solution was heated at 95° C. for 24 hours, with a constant stream of argon gas being passed through the apparatus to remove the HCl liberated. Via a T-piece at the top of the condenser, the HCl-containing stream of argon was passed into an alcoholic KOH solution. After the reaction was complete, the toluene and any traces of PCl₃ present were taken off, giving a brown oil. After addition of 10 ml of fresh toluene, the product was dried by means of a high vacuum pump, giving a dry brown powder. The phosphonite obtained was stored under argon in a Schlenk tube at −20° C. The yield of the light-brown powder was 100% of theory.

Preparation of Ligand D

This was prepared by reacting 9,9-dimethylxanthene with dibenzo[d,f]-2,2'-di-tert-butyl-4,4'-dimethoxy-[1,3,2]-dioxaphosphochloride.

II. Hydroformylations

Example 1
Hydroformylation of 1-octene Using Ligand A 0.79 mg of dicarbonylrhodium acetylacetonate and 16.5 mg of ligand A (60 ppm of Rh, ligand/metal ratio=6.1:1) were weighed out separately, each dissolved in 1.3 g of toluene, mixed and treated at 100° C. with a synthesis gas mixture of CO/H₂ (1:1) at 10 bar in a 300 ml steel autoclave provided with a sparging stirrer. After 30 minutes, the autoclave was depressurized, 2.6 g of 1-octene were then added and the mixture was hydroformylated at 100° C. and 10 bar for another 4 hours. The conversion was 98%, the aldehyde selectivity was 48% and the linearity was 81%. The proportion of a-isomers (n-aldehyde and isoaldehyde) was 96%.

Example 2
Hydroformylation of 2-butene Using Ligand A 3 mg of dicarbonylrhodium acetylacetonate and 63.4 mg of ligand A (60 ppm of Rh, ligand/metal ratio=6.2:1) were weighed out separately, each dissolved in 5 g of toluene, mixed and treated at 100° C. with a synthesis gas mixture of CO/H₂ (1:1) at 10 bar in a 300 ml steel autoclave provided with a sparging stirrer. After 30 minutes, the autoclave was cooled and depressurized, 10 g of 2-butene were then injected and a pressure of 5 bar of CO/H₂ (1:1) was set at ambient temperature. The autoclave was subsequently heated to 140° C. and hydroformylation was carried out for 4 hours. During the reaction, further synthesis gas was introduced to maintain a constant pressure. After the reaction was complete, the autoclave was depressurized, with the gas released being passed through a cold trap and the products from the reactor and the cold trap being analyzed by means of gas chromatography. The aldehyde selectivity was 93% and the linearity was 69%.

Example 3
Hydroformylation of 1-octene Using Ligand B

The procedure of Example 1 was repeated using 0.79 mg of dicarbonylrhodium acetylacetonate and 16.6 mg of ligand B (60 ppm of Rh, ligand/metal ratio=5:1), each in 1.3 g of toluene, and 2.6 g of 1-octene for the hydroformylation. The conversion was 99%, the aldehyde selectivity was 91% and the linearity was 88%. The proportion of a product was 98%.

Example 4
Hydroformylation of 1-octene Using Ligand B

The procedure of Example 1 was repeated using 0.79 mg of dicarbonylrhodium acetylacetonate and 16.6 mg of ligand B (60 ppm of Rh, ligand/metal ratio=5:1), each in 1.3 g of toluene, and 2.6 g of 1-octene for the hydroformylation. The temperature during the hydroformylation was 80° C. The conversion was 97%, the aldehyde selectivity was 90% and the linearity was 90%. The proportion of a product was 100%.

Example 5
Hydroformylation of 2-butene Using Ligand B

The procedure of Example 2 was repeated using 3 mg of dicarbonylrhodium acetylacetonate and 126 mg of ligand B (60 ppm of Rh, ligand/metal ratio=9.9:1), each in 5 g of toluene, and 10 g of 2-butene for the hydroformylation. The conversion was 66%, the aldehyde selectivity was 94% and the linearity was 66%.

Example 6
Hydroformylation of 1-octene Using Ligand C

The procedure of Example 1 was repeated using 0.93 mg of dicarbonylrhodium acetylacetonate and 19.6 mg of ligand C (60 ppm of Rh, ligand/metal ratio=5:1), each in 1.55 g of xylene, and 3.1 g of 1-octene were used for the hydroformylation. The temperature during the hydroformylation was 90° C. The conversion was 89% and the linearity was 81%. The proportion of a products was 100%.

Example 7
Hydroformylation of 1-octene Using Ligand D

The procedure of Example 1 was repeated using 0.78 mg of dicarbonylrhodium acetylacetonate and 14.9 mg of ligand D (60 ppm of Rh, ligand/metal ratio=5:1), each in 1.3 g of xylene, and 2.6 g of 1-octene for the hydroformylation. The temperature during the hydroformylation was 80° C. The conversion was 53%, the aldehyde selectivity was 30% and the linearity was 82%. The proportion of a product was 100%.

Example 8
Hydroformylation of 1-octene Using Ligand E

The procedure of Example 1 was repeated using 0.87 mg of dicarbonylrhodium acetylacetonate and 17.1 mg of ligand E (60 ppm of Rh, ligand/metal ratio=5:1), each in 1.45 g of xylene, and 2.9 g of 1-octene for the hydroformylation. The temperature during the hydroformylation was 90° C. The conversion was 49%, the aldehyde selectivity was 94% and the linearity was 88%. The proportion of a product was 100%.

Example 9
Hydroformylation of 1-octene Using Ligand F

The procedure of Example 1 was repeated, except that ligand F was used instead of ligand A, the molar ratio of carbon monoxide to hydrogen was 1:2, the temperature was 90° C., the pressure was 5 bar, the reaction time was 4 hours. The conversion was 36%, the aldehyde selectivity was 47% and the linearity was 96%.

Example 10
Hydroformylation of 1-octene Using Ligand F

The procedure of Example 1 was repeated, except that ligand F was used instead of ligand A, the molar ratio of carbon monoxide to hydrogen was 1:2, the temperature was 120° C., the pressure was 10 bar, the reaction time was 4 hours. The conversion was 92%, the aldehyde selectivity was 33% and the linearity was 94%.

We claim:

1. A process for the hydroformylation of compounds containing at least one ethylenically unsaturated double bond by reaction with carbon monoxide and hydrogen in the presence of a hydroformylation catalyst comprising at least one complex of a metal of transition group VIII with at least one ligand selected from among compounds of the general formula I

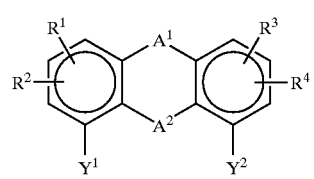

where
- $A^1$ and $A^2$ are each, independently of one another, O, S, $SiR^aR^b$, $NR^c$ or $CR^5R^6$, where
  - $R^a$, $R^b$, $R^c$, $R^5$ and $R^6$ are each, independently of one another, hydrogen, alkyl, cycloalkyl, heterocycloalkyl, aryl or hetaryl,
- $Y^1$ and $Y^2$ are each, independently of one another, radicals containing at least one phosphorus, arsenic or antimony atom, where in each case at least two substituted or unsubstituted heteroatoms selected from among O, S and $NR^c$, where $R^c$ is hydrogen, alkyl, cycloalkyl or aryl, are directly bound to the phosphorus, arsenic or antimony atom, and
- $R^1$, $R^2$, $R^3$ and $R^4$ are each, independently of one another, hydrogen, alkyl, cycloalkyl, heterocycloalkyl, aryl, hetaryl, $COOR^d$, $COO^-M^+$, $SO_3R^d$, $SO^-_3M^+$, $NE^1E^2$, $NE^1E^2E^{3+}X^-$, alkylene-$NE^1E^2E^{3+}X^-$, $OR^d$, $SR^d$, $(CHR^eCH_2O)_xR^d$, $(CH_2N(E^1))_xR^d$, $(CH_2CH_2N(E^1))_xR^d$, halogen, trifluoromethyl, nitro, acyl or cyano, where
  - $R^d$, $E^1$, $E^2$ and $E^3$ are identical or different radicals selected from among hydrogen, alkyl, cycloalkyl and aryl,
  - $R^e$ is hydrogen, methyl or ethyl,
  - $M^+$ is a cation,
  - $X^-$ is an anion, and
  - x is an integer from 1 to 120, or
- $R^1$ and/or $R^3$ together with two adjacent carbon atoms of the benzene ring to which they are bound form a fused ring system having 1, 2 or 3 further rings.

2. A process as claimed in claim 1, wherein, in the formula I, $Y^1$ and $Y^2$ are each, independently of one another, a radical of the formula $P(OR^7)(OR^8)$, $OP(OR^7)R^8$ or $OP(OR^7)(OR^8)$, where
- $R^7$ and $R^8$ are each, independently of one another, alkyl, cycloalkyl, heterocycloalkyl, aryl or hetaryl which may bear one, two or three substituents selected from among alkyl, cycloalkyl, heterocycloalkyl, aryl, hetaryl, $COOR^f$, $COO^-M^+$, $SO_3R^f$, $SO^-_3M^+$, $NE^4E^5$, alkylene-$NE^4E^5$, $NE^4E^5E^{6+}X^-$, alkylene-$NE^4E^5E^{6+}X^-$, $OR^f$, $SR^f$, $(CHR^gCH_2O)_yR^f$, $(CH_2N(E^4))_yR^f$, $(CH_2CH_2N(E^4))_yR^f$, halogen, trifluoromethyl, nitro, acyl and cyano, where
  - $R^f$, $E^4$, $E^5$ and $E^6$ are identical or different radicals selected from among hydrogen, alkyl, cycloalkyl or aryl,
  - $R^g$ is hydrogen, methyl or ethyl,
  - $M^+$ is a cation,
  - $X^-$ is an anion, and
  - y is an integer from 1 to 120, or
- $R^7$ and $R^8$ together with the phosphorus atom and the oxygen atom(s) to which they are bound form a 5- to 8-membered heterocycle to which one, two or three cycloalkyl, heterocycloalkyl, aryl or hetaryl groups may additionally be fused, where the heterocycle and, if present, the fused-on groups may each bear, independently of one another, one, two, three or four substituents selected from among alkyl, cycloalkyl, heterocycloalkyl, aryl, hetaryl, $COOR^f$, $COO^-M^+$, $SO_3R^f$, $SO^-_3M^+$, $NE^4E^5$, alkylene-$NE^4E^5$, $NE^4E^5E^{6+}X^-$, alkylene-$NE^4E^5E^{6+}X^-$, $OR^f$, $SR^f$, $(CHR^gCH_2O)_yR^f$, $(CH_2N(E^4))_yR^f$, $(CH_2CH_2N(E^4))_yR^f$, halogen, trifluoromethyl, nitro, acyl and cyano, where $R^f$, $R^g$, $E^4$, $E^5$, $E^6$, $M^+$, $X^-$ and y are as defined above.

3. A process as claimed in claim 1, wherein the compound of the formula I is selected from among compounds of the formulae I.1 to I.6

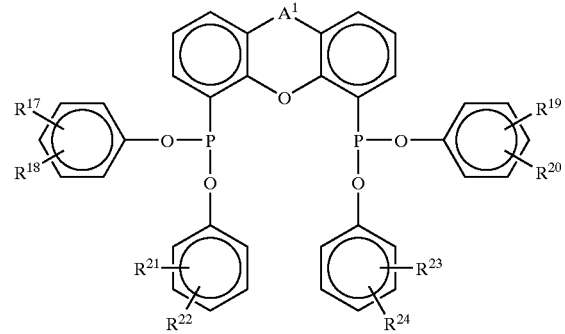

(I.1)

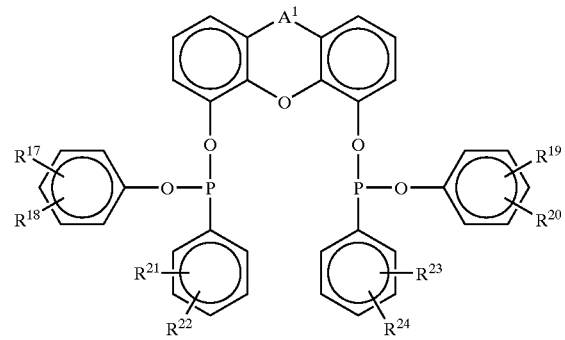

(I.2)

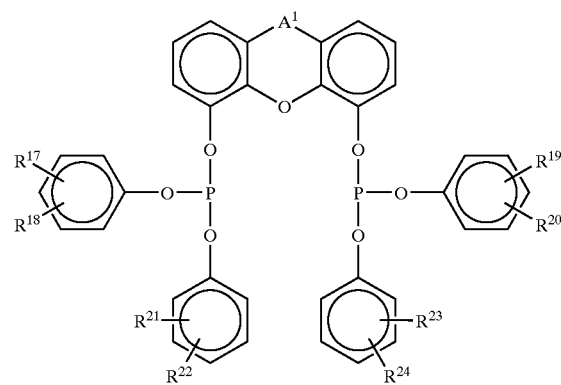

(I.3)

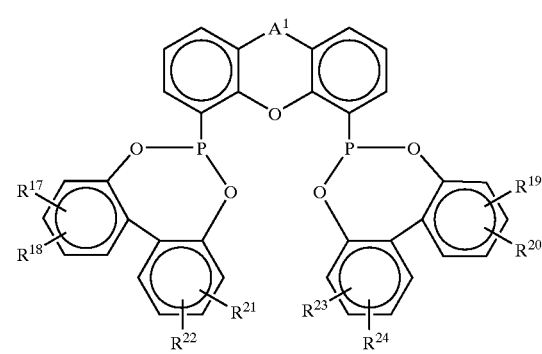

(I.4)

-continued

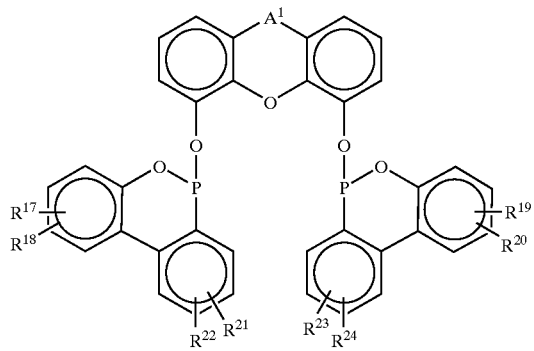

(I.5)

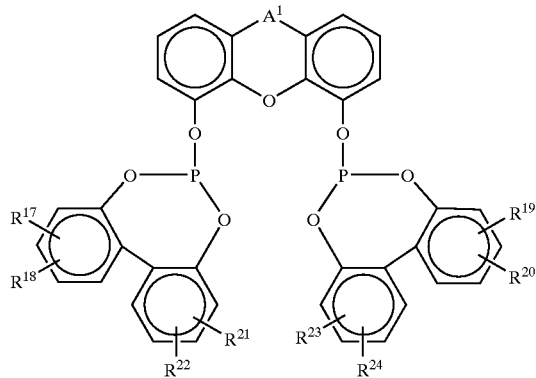

(I.6)

$A^1$ is O, S or $CR^5R^6$, where $R^5$ and $R^6$ are each, independently of one another, hydrogen or $C_{1-C4}$-alkyl, $R^{17}$, $R^{18}$, $R^{19}$, $R^{20}$, $R^{21}$, $R^{22}$, $R^{23}$ and $R^{24}$ are each, independently of one another, hydrogen, alkyl, cycloalkyl, heterocycloalkyl, aryl, hetaryl, $COOR^f$, $COO^-M^+$, $SO_3R^f$, $SO^-_3M^+$, $NE^4E^5$, alkylene-$NE^4E^5$, $NE^4E^5E^{6+}X^-$, alkylene-$NE^4E^5E^{6+}X^-$, $OR_f$, $SR^f$, $(CHR^gCH_2O)_yR^f$, $(CH_2N(E^4))_yR^f$, $(CH_2CH_2N(E^4))_yR^f$, halogen, trifluoromethyl, nitro, acyl and cyano, where $R^f$, $E^4$, $E^5$ and $E^6$ are identical or different radicals selected from among hydrogen, alkyl, cycloalkyl and aryl, $R^g$ is hydrogen, methyl or ethyl, $M^+$ is a cation, $X^-$ is an anion, and y is an integer from 1 to 120.

4. A process as claimed in claim 2, wherein the metal of transition group VIII is selected from among cobalt, ruthenium, iridium, rhodium, palladium and platinum.

5. A process as claimed in claim 3, wherein the catalyst further comprises at least one additional ligand selected from among halides, amines, carboxylates, acetylacetonate, arylsulfonates and alkylsulfonates, hydride, CO, olefins, dienes, cycloolefins, nitriles, N-containing heterocycles, aromatics and heteroaromatics, ethers, $PF_3$, phospholes, phosphabenzenes and monodentate, bidentate and polydentate phosphine, phosphinite, phosphonite, phosphoramidite and phosphite ligands.

6. A process as claimed in claim 4, wherein the unsaturated compound used for the hydroformylation is selected from among internal linear olefins and olefin mixtures in which at least one internal linear olefin is present.

* * * * *

UNITED STATES PATENT AND TRADEMARK OFFICE
CERTIFICATE OF CORRECTION

PATENT NO. : 6,881,867 B2
DATED : April 19, 2005
INVENTOR(S) : Ahlers et al.

It is certified that error appears in the above-identified patent and that said Letters Patent is hereby corrected as shown below:

Column 23,
Line 35, "$C_{1-C4}$-alkl" should read -- $C_1$-$C_4$-alkl --.

Signed and Sealed this

Sixth Day of December, 2005

JON W. DUDAS
*Director of the United States Patent and Trademark Office*

UNITED STATES PATENT AND TRADEMARK OFFICE
CERTIFICATE OF CORRECTION

PATENT NO. : 6,881,867 B2
DATED : April 19, 2005
INVENTOR(S) : Ahlers et al.

It is certified that error appears in the above-identified patent and that said Letters Patent is hereby corrected as shown below:

Column 23,
Line 36, "$C_1$-$C_4$-alkl" should read -- $C_1$-$C_4$-alkyl --.

Column 24,
Line 6, "$OR_f$" should read -- $OR^f$ --.

Signed and Sealed this

Twenty-first Day of February, 2006

JON W. DUDAS
*Director of the United States Patent and Trademark Office*